(12) United States Patent
Yardimci et al.

(10) Patent No.: US 10,632,252 B2
(45) Date of Patent: Apr. 28, 2020

(54) SUBCUTANEOUS INFUSION DEVICE FOR INJECTING MEDICINAL SUBSTANCES

(71) Applicants: Baxalta Incorporated, Bannockburn, IL (US); Baxalta GmbH, Glattpark (Opfikon) (CH)

(72) Inventors: Atif Mehmet Yardimci, Lake Forest, IL (US); Aaron Tan, Cleveland, MS (US); Tejas J. Dhyani, Grayslake, IL (US); Nathan A. Mitchell, Volo, IL (US); Eric Bernard Jedrzejek, Lake Forest, IL (US); Chinmay Kanuga, Porter Ranch, CA (US)

(73) Assignees: Baxalta Incorporated, Bannockburn, IL (US); Baxalta GmbH, Glattpark (Opfikon) (CH)

( * ) Notice: Subject to any disclaimer, the term of this patent is extended or adjusted under 35 U.S.C. 154(b) by 0 days.

(21) Appl. No.: 15/300,020

(22) PCT Filed: Mar. 25, 2015

(86) PCT No.: PCT/US2015/022494
§ 371 (c)(1),
(2) Date: Sep. 28, 2016

(87) PCT Pub. No.: WO2015/148667
PCT Pub. Date: Oct. 1, 2015

(65) Prior Publication Data
US 2017/0165419 A1  Jun. 15, 2017

Related U.S. Application Data

(60) Provisional application No. 61/971,966, filed on Mar. 28, 2014.

(51) Int. Cl.
*A61M 5/158* (2006.01)
*A61M 39/28* (2006.01)
(Continued)

(52) U.S. Cl.
CPC .......... *A61M 5/158* (2013.01); *A61M 5/3202* (2013.01); *A61M 5/3243* (2013.01);
(Continued)

(58) Field of Classification Search
CPC .. A61M 2005/1581; A61M 2005/1583; A61M 2005/1586; A61M 2005/1587;
(Continued)

(56) References Cited

U.S. PATENT DOCUMENTS 3,538,915 A    11/1970  Frampton et al.
3,589,361 A *   6/1971  Loper ................... A61M 25/02
                                              604/165.03

(Continued)

FOREIGN PATENT DOCUMENTS

CN       1649637 A      8/2005
CN       1878584 A     12/2006
(Continued)

OTHER PUBLICATIONS

Written Opinion for PCT/US2015/022494 dated Jul. 30, 2015.
(Continued)

*Primary Examiner* — Quynh-Nhu H. Vu
(74) *Attorney, Agent, or Firm* — Wolf, Greenfield & Sacks, P.C.

(57) ABSTRACT

A medical delivery device is provided for delivering a medicinal substance into a user's body. A foldable hub has a left wing and a right wing, where the hub is attached at one end to a tube, and at an opposite end to a needle. At least one first rib is disposed on the left wing and at least one second rib is disposed on the right wing. When the wings are folded back away from the needle and pinched together, the first and second ribs prevent twisting and/or sliding of the wings relative to each other during an insertion of the needle into
(Continued)

a user's skin, thereby preventing a breakage of the needle due to undesirable movement of the wings.

15 Claims, 5 Drawing Sheets

(51) Int. Cl.
*A61M 39/20* (2006.01)
*A61M 5/32* (2006.01)

(52) U.S. Cl.
CPC .......... *A61M 5/3275* (2013.01); *A61M 39/20* (2013.01); *A61M 39/28* (2013.01); *A61M 2005/1581* (2013.01); *A61M 2005/1583* (2013.01); *A61M 2005/1586* (2013.01); *A61M 2005/1587* (2013.01)

(58) Field of Classification Search
CPC ...... A61M 39/20; A61M 39/28; A61M 5/158; A61M 5/3202; A61M 5/3243; A61M 5/3275
See application file for complete search history.

(56) References Cited

U.S. PATENT DOCUMENTS

| | | | | |
|---|---|---|---|---|
| 3,640,275 A * | 2/1972 | Burke | ............... | A61M 25/0637 604/177 |
| 3,670,727 A * | 6/1972 | Reiterman | ............ | A61M 5/158 604/177 |
| 4,698,057 A * | 10/1987 | Joishy | .................. | A61M 25/02 128/DIG. 26 |
| 4,710,175 A * | 12/1987 | Cartmell | ........... | A61M 25/0014 604/177 |
| 4,834,708 A * | 5/1989 | Pillari | ............... | A61M 25/0637 604/165.04 |
| 4,867,172 A * | 9/1989 | Haber | ................. | A61M 5/3129 600/576 |
| 5,149,328 A * | 9/1992 | Zaha | ................. | A61M 25/0637 604/174 |
| 5,306,253 A * | 4/1994 | Brimhall | ........... | A61M 25/0637 604/165.03 |
| 5,380,293 A * | 1/1995 | Grant | ................ | A61M 25/0631 604/177 |
| 5,584,813 A * | 12/1996 | Livingston | ........ | A61M 25/0637 604/177 |
| 6,500,155 B2 * | 12/2002 | Sasso | .................... | A61M 5/158 604/177 |
| 6,911,020 B2 * | 6/2005 | Raines | .................. | A61M 5/158 604/177 |
| 6,997,902 B2 * | 2/2006 | Thorne | ................ | A61M 5/158 604/110 |
| 7,776,016 B1 * | 8/2010 | Halseth | ................ | A61M 5/158 604/162 |
| 2001/0011164 A1 * | 8/2001 | Bierman | ............... | A61M 25/02 604/180 |
| 2002/0099360 A1 * | 7/2002 | Bierman | ............... | A61M 39/10 604/523 |
| 2002/0111581 A1 * | 8/2002 | Sasso | .................... | A61M 5/158 604/93.01 |
| 2003/0163096 A1 | 8/2003 | Swenson et al. | | |
| 2006/0047252 A1 * | 3/2006 | Ono | .................... | A61M 5/158 604/263 |
| 2009/0187153 A1 | 7/2009 | West et al. | | |
| 2010/0010451 A1 * | 1/2010 | Kashmirian | .......... | A61M 5/158 604/192 |
| 2012/0041253 A1 | 2/2012 | Wu et al. | | |

FOREIGN PATENT DOCUMENTS

| | | |
|---|---|---|
| GB | 2014045 A | 3/1979 |
| WO | WO 2005/049109 A2 | 6/2005 |
| WO | WO 2007/137339 A1 | 12/2007 |
| WO | WO 2013/139476 A1 | 9/2013 |

OTHER PUBLICATIONS

PCT Search Report for PCT/US2015/022494 dated Jul. 30, 2015.
European Examination Report dated Sep. 20, 2018 in connection with European Application No. 15715591.2.
Chinese Office Action dated Jun. 4, 2019 in connection with Chinese Application No. 201580017380.2.

* cited by examiner

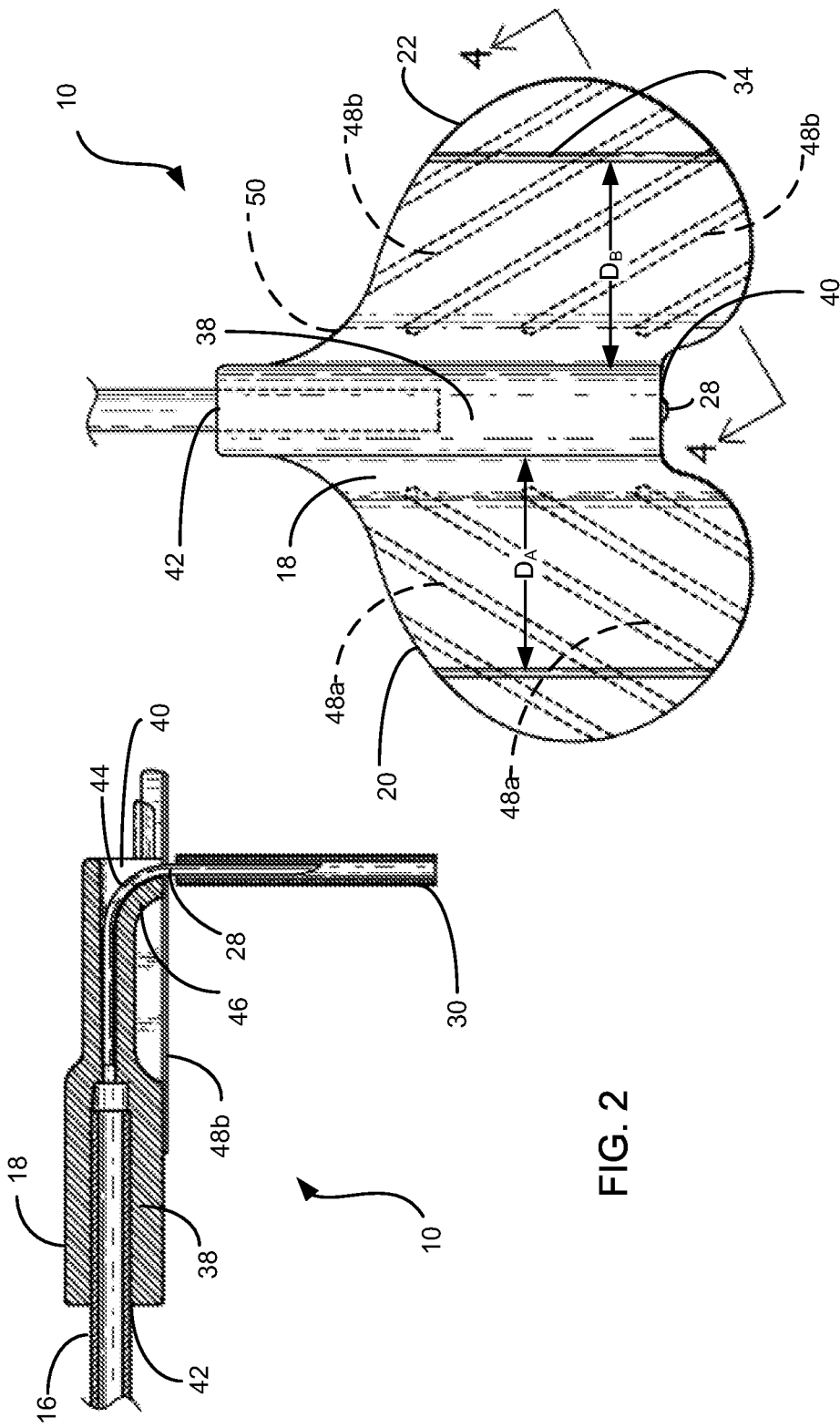

SUBCUTANEOUS INFUSION DEVICE FOR INJECTING MEDICINAL SUBSTANCES

CROSS REFERENCE

The present application is a 35 U.S.C. § 371 National Stage application which claims priority to International Application No. PCT/US2015/022494 filed on Mar. 25, 2015 under 35 U.S.C. §§ 119(a) and 365(b), which claims priority to a U.S. provisional patent application Ser. No. 61/971,966 filed on Mar. 28, 2014 under 35 U.S.C. § 119(e); both of which applications are incorporated herein by reference.

BACKGROUND

The present disclosure generally relates to devices for injecting medicinal substances, and more particularly relates to a medical fluid delivery device for subcutaneously administering viscous liquid medicines into the body of a user.

Subcutaneous infusion devices are well known in the medical arts for use in the administration of a selected medicinal substance to a desired infusion site located underneath the skin of a patient or user. Commonly included in such infusion device is a tubular cannula or catheter that is supported by and protrudes from a hub for receiving the medicinal substance via a delivery tubing. Typically, the hub includes a small needle that is inserted just under the surface of the skin, and remains in place for up to several days.

More specifically, such infusion devices provide an alternative to intravenous delivery of medicines and allow the medicinal substance to be administered through a layer of skin immediately below the dermis and epidermis. As is known in the art, such use of the subcutaneous infusion devices decreases the number of times the patient must have an injection to receive frequently administered medicines. Although not all medicines can be administered through such infusion devices, they are an effective and convenient way to administer medicinal substances without having to impose multiple injections on the patient.

However, some medicinal substances are highly viscous (i.e., in the range of 3-10 cP or centipoise) and are delivered at high flow rates, and conventional subcutaneous infusion devices are not designed to deliver the highly viscous substance at these flow rates. As a result, a build-up of excessive delivery pressure during the delivery of such substances is likely to occur, and clogging may occur in the needle or its adjacent areas during infusion. Further, because the needle used in the infusion device is typically bent about 90 degrees, the risk of kinking is relatively high at or near the bent portion of the needle.

Another issue of conventional infusion devices is that movement of the hub can cause the needle to break during use. Foldable gripping wings are typically attached to the hub for securely holding the needle when inserting the needle straight into the desired infusion site at a 90 degree angle relative to the skin surface. Specifically, the wings are folded back away from the needle and pinched together between two fingers. At times, the folded wings slide against each other during the insertion step, making the insertion of the needle rather challenging. Further, if the needle is made of a smaller diameter, the needle is not supported firmly and causes it to break during use.

Therefore, there is a need for improving subcutaneous infusion devices to facilitate a more stable retention of the needle on the skin during the insertion step, and for reducing flow resistance of highly viscous substance during the delivery step.

SUMMARY

The present disclosure is directed to a medical fluid delivery device for subcutaneously administering viscous liquid medicines into the body of a user or patient. The present infusion device is designed to reduce a pressure drop (or flow resistance) that occurs during the delivery step of the viscous liquid or solution into a subcutaneous space of the user's skin. As described in further detail below, the present infusion device delivers the viscous liquid at a higher flow rate than the conventional devices due to the geometry of a hub and a needle.

One aspect of the present infusion device is that low flow resistance is achieved for high viscosity liquids (e.g., 3-20 cP) in flow rates ranging 40 to 400 ml/hr (or milliliter/hour) during subcutaneous delivery. Specifically, a 24 G (or gauge) needle having a thin tubular wall is provided for accommodating the viscous liquid, and a mid-region of the needle is slightly bent at a predetermined radius of curvature, such that the mid-region surrounds a support region located at an outer end of the hub.

Another important aspect is that the present infusion device provides secure placement of the needle that reduces disturbance to the desired infusion site, and enhances comfort during infusion. A plurality of substantially diagonally disposed ribs is provided on a bottom side of the hub for preventing unwanted movement of the hub while worn by the user. More specifically, the diagonal bottom ribs are angled in such a manner that a forward movement toward the sharp end of the needle is prevented while a backward movement away from the sharp end of the needle is allowed. Furthermore, the diagonal pattern also stabilizes the hub for lateral disturbances after installation of the needle. This arrangement reduces shear and/or normal stress on the bent portion of the needle.

Yet another aspect of the present device is that a top side of the hub includes at least two ribs, each one of which is respectively located on a left wing and a right wing of the hub. Each rib is asymmetrically disposed on the wings, such that when the wings are folded back away from the needle and pinched together, the two ribs prevent twisting and/or sliding of the wings relative to each other during an insertion of the needle into the skin. Accordingly, the needle remains stable and straight during the insertion, preventing a breakage of the needle due to undesirable movement of the wings.

BRIEF DESCRIPTION OF THE DRAWINGS

FIG. 2 is a vertical cross-section taken along the line 2-2 of FIG. 1 and in the direction generally indicated;

FIG. 3 is a top view of the present hub featuring angled bottom ribs;

DETAILED DESCRIPTION

Figure 1:
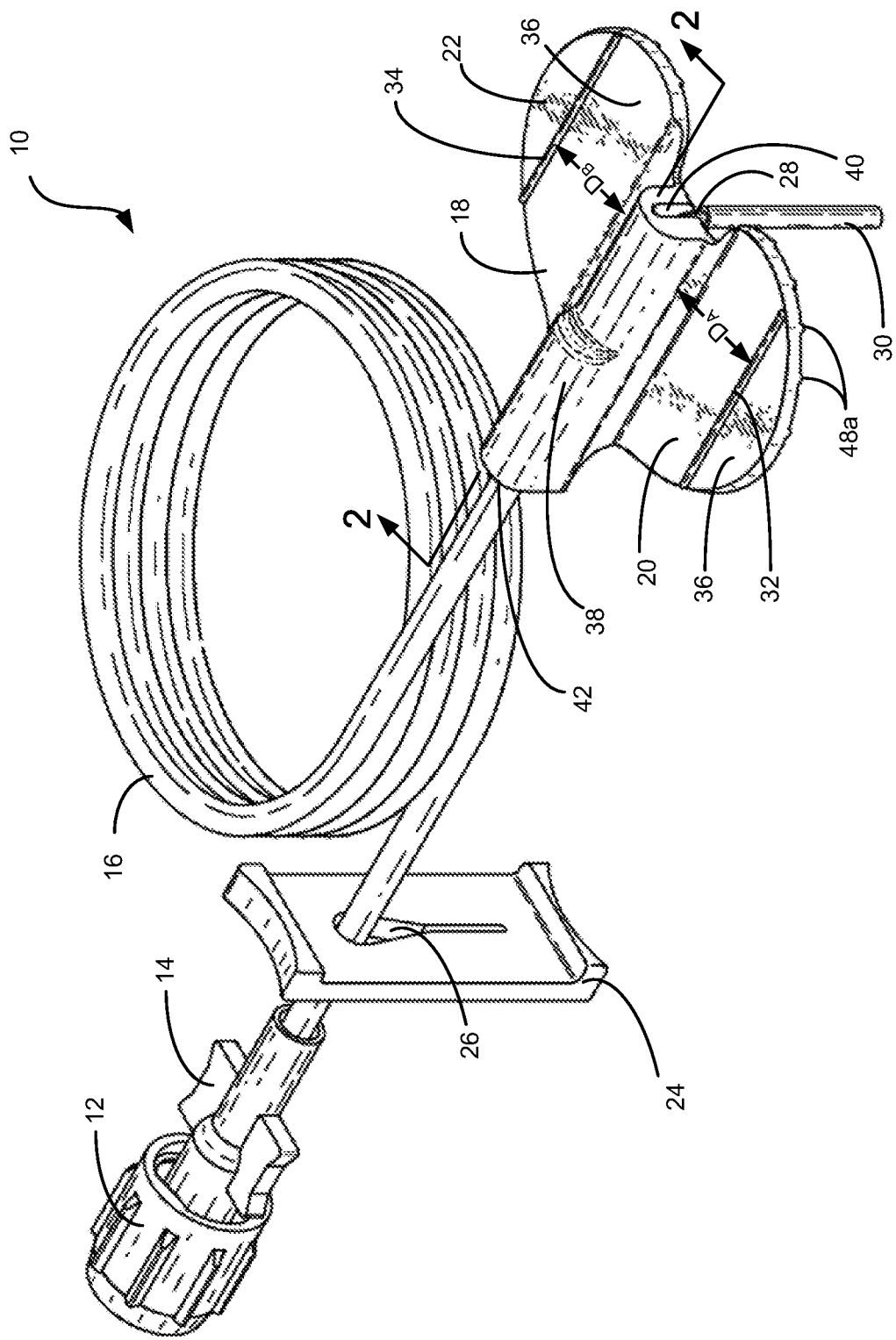
FIG. 1 is a top perspective view of the present infusion device featuring a winged hub having top ribs.

Referring now to FIGS. 1-2, the present subcutaneous infusion device is generally designated 10 and is designed for subcutaneously delivering a medicinal substance below the dermis and epidermis. An exemplary medicinal substance may include nutritional products and Chinese herbal medicinal products. It is contemplated that the device 10 is disposable. Included in the device 10 is a luer cap 12 configured for receiving the liquid at one end, and at an opposite end, is attached to a female luer connector 14 using complementary helically threaded portions for threadably fastening the cap and connector together. For carrying a viscous liquid medicine to an infusion site, a flexible elongated tube 16 is attached at one end to the female luer connector 14, and at an opposite end to a foldable hub 18 having a left or first wing 20 and a right or second wing 22.

An exemplary length of the tube 16 is approximately 24 inches, but it is also contemplated that any length of tube can be utilized to suit different applications. Regulating a flow of the viscous liquid medicine in the tube 16 is achieved by transversely adjusting a slide clamp 24 relative to a longitudinal axis of the tube. As an example, a movable release slot 26 is provided in a center of the slide clamp 24 such that the clamp can transition between an occluding position and a non-occluding position by selectively sliding the release slot relative to the tube 16.

In a preferred embodiment, the winged hub 18 is molded, as by injection molding or the like, such that the hub and its connecting elements are integrally formed. However, it is also contemplated that the hub 18 is attachable to the connecting elements by chemical adhesives, solvent boding, ultrasonic welding or other conventional fastening techniques. More specifically, the hub 18 is attached at one end to the tube 16, and at an opposite end to a needle 28, which is slidably fitted into and safeguarded by a needle protector 30 when not in use. It is contemplated that after the hub 18 is molded, the needle 28 is assembled onto the hub 18 using an adhesive. Alternatively, the hub 18 may be over-molded over the needle 28.

An exemplary needle size is approximately 24 G for ensuring comfort during infusion, and an exemplary needle length may be one of 6, 9, or 12 mm (or millimeter) depending on an application. Preferably, the needle 28 has a thin tubular wall for accommodating the viscous liquid medicine.

An important aspect of the present hub 18 is that each of the foldable left and right wings 20, 22 of the hub has at least one top rib 32, 34 extending along an entire longitudinal length of a corresponding wing. Each top rib 32, 34 is disposed on an upper surface 36 of the corresponding wing 20, 22, such that when the wings are folded, the top ribs 32, 34 are directly in contact with the upper surface 36 of a corresponding opposite wing. As a result, the top rib 32 disposed on the left wing 20 engages the upper surface 36 of the right wing 22, and conversely the top rib 34 disposed on the right wing 22 engages the upper surface 36 of the left wing 20.

Figure 5:
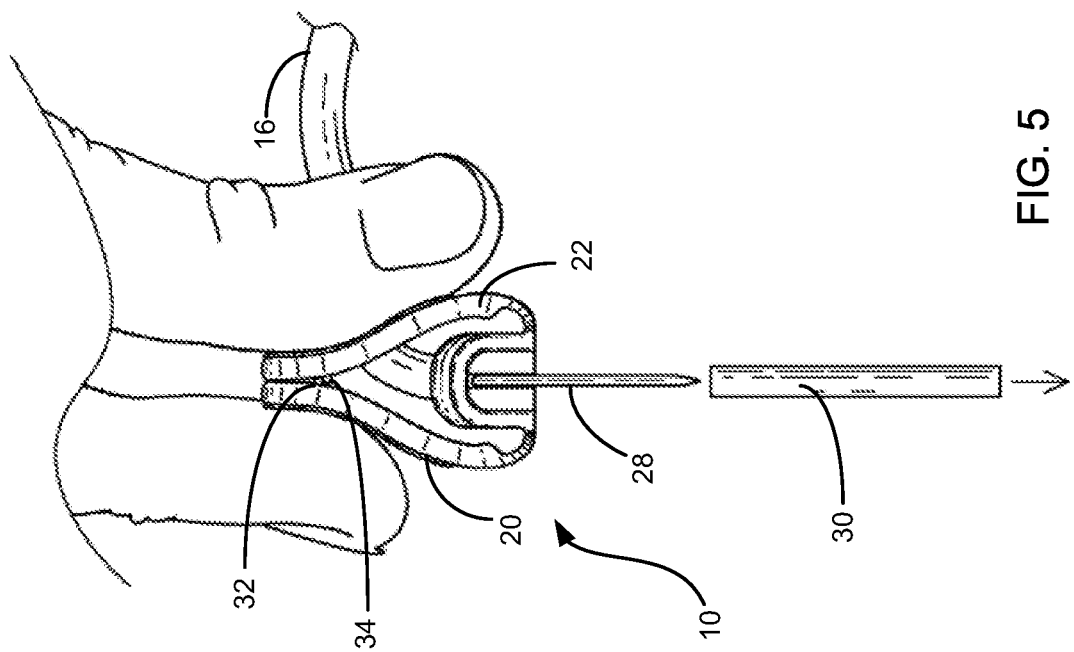
FIG. 5 is a front view of the winged hub folded away from a needle in preparation of an insertion of the needle into an infusion site.
Figure 4:
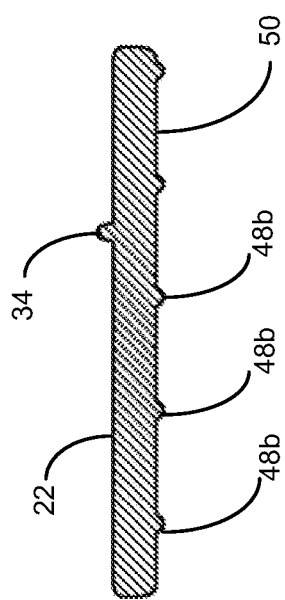
FIG. 4 is a vertical cross-section taken along the line 4-4 of FIG. 3 and in the direction generally indicated.

As illustrated in an exemplary FIGS. 1 and 5 embodiment, a left or first top rib 32 is asymmetrically disposed from a right or second top rib 34 such that the first top rib 32 is juxtaposed with the second top rib 34 when the wings 20, 22 are folded back away from the needle 28 and pinched together (FIG. 5). More specifically, the first top rib 32 is spaced in parallel from an elongated center section 38 of the hub 18 at a first predetermined distance $D_A$ (FIG. 1), but the second top rib 34 is spaced in parallel from the center section at a second predetermined distance $D_B$ (FIG. 1), where the first distance $D_A$ is different from the second distance $D_B$.

For example, as best shown in the FIG. 5 embodiment, the first distance $D_A$ is longer than the second distance $D_B$, and the first rib 32 goes over the second rib 34 such that the ribs 32, 34 are adjacently positioned with each other when the wings 20, 22 are folded back. As a result, this particular configuration of the top ribs 32, 34 prevents the wings 20, 22 from twisting or sliding relative to each other, thereby reducing the risk of breakage of the needle 28 during the insertion of the needle into the skin.

Returning now to FIGS. 1-2, a first insertion opening 40 at a first end of the center section 38 is configured for accommodating insertion of the needle 28, and a second insertion opening 42 at a second opposite end of the center section in fluid communication with the tube 16 is configured for accommodating insertion of the tube. In a preferred embodiment, the tube 16 is inserted into the first insertion opening 40 approximately half a length of the center section 38 to reduce a total length of the needle 28 (FIG. 2).

Both openings 40, 42 provide a passage way for the delivery of the liquid medicine. This passage way provides low flow resistance for high viscosity liquids (e.g., 3-20 cP) in flow rates ranging 40 to 400 ml/hr during subcutaneous delivery without dropping a fluid pressure more than 10 psi (or pounds per square inch). More specifically, an exemplary 24 G stainless needle 28 having the thin tubular wall is configured for accommodating the viscous liquid medicine, and a mid-region 44 of the needle 28 is slightly bent at a predetermined radius of curvature (e.g., 0.125" typically and not less than 0.060" or more than 0.200"), such that the mid-region of the needle surrounds a support region 46 located at or near the first insertion opening 40 of the center section 38.

It is preferred that the mid-region 44 of the needle 28 is bent gradually at an angle of 45 to 90 degrees (nominally close to 90 degrees), such that the support region 46 buttresses against the bent mid-region of the needle. A sharp end of the needle 28 extends outwardly from the first insertion opening 40 of the center section 38 so that the sharp end of the needle is disposed transverse to a longitudinal axis of the center section. Consequently, the support region 46 reduces the risk of needle breakage, and provides integrated support for the bent mid-region 44 not only during the insertion of the needle 28 into the skin but also while being attached to the user's body.

Referring now to FIGS. 2-4 and 8, a plurality of substantially diagonally disposed bottom ribs 48a, 48b is provided on a lower or bottom surface 50 of each wing 20, 22 for preventing unwanted movement of the hub 18 during use. It is preferred that the bottom ribs 48a, 48b are generally evenly spaced in parallel, and extend along a full diagonal length of a corresponding wing 20, 22. The bottom ribs 48a, 48b are angled or slanted in such a manner that a forward movement toward the sharp end of the needle 28 is prevented, while a backward movement away from the sharp end of the needle is allowed. This particular arrangement reduces shear and/or normal stress on the bent mid-region 44 of the needle 28 during use.

In a preferred embodiment, both the first and second wings 20, 22 of the hub 18 have the bottom ribs 48a, 48b positioned on the lower surface 50 at an angle of approximately 45 degrees relative to the longitudinal axis of the center section 38. An important aspect of the ribs 48a, 48b is, however, that each bottom rib 48a disposed on the lower surface 50 of the first wing 20 is inclined or sloped upwardly from a left side of the first wing to a right side of the first wing toward the center section 38. In a mirrored orientation, each bottom rib 48b disposed on the lower surface 50 of the second wing 22 is declined or sloped downwardly from a left side of the second wing adjacent the center section 38 to a right side of the second wing. As a whole, the bottom ribs 48a, 48b are constructed and arranged in a chevron or herringbone pattern, thereby preventing unwanted movement of the hub 18 while being attached to the user's body.

This enhanced friction provided by the ribs 48a, 48b prevents slippage of the hub 18 from the skin during use. While diagonally arranged ribs 48a, 48b are shown for illustration purposes, any type of knurling or textured ribs, ridges, grooves, or bumps are contemplated for disposition as a friction formation on the lower surface 50 of the wings 20, 22 for enhancing friction in this manner. Further, the angular orientation and/or spacing of the ribs 48a, 48b is variable to suit the situation.

Figure 7:
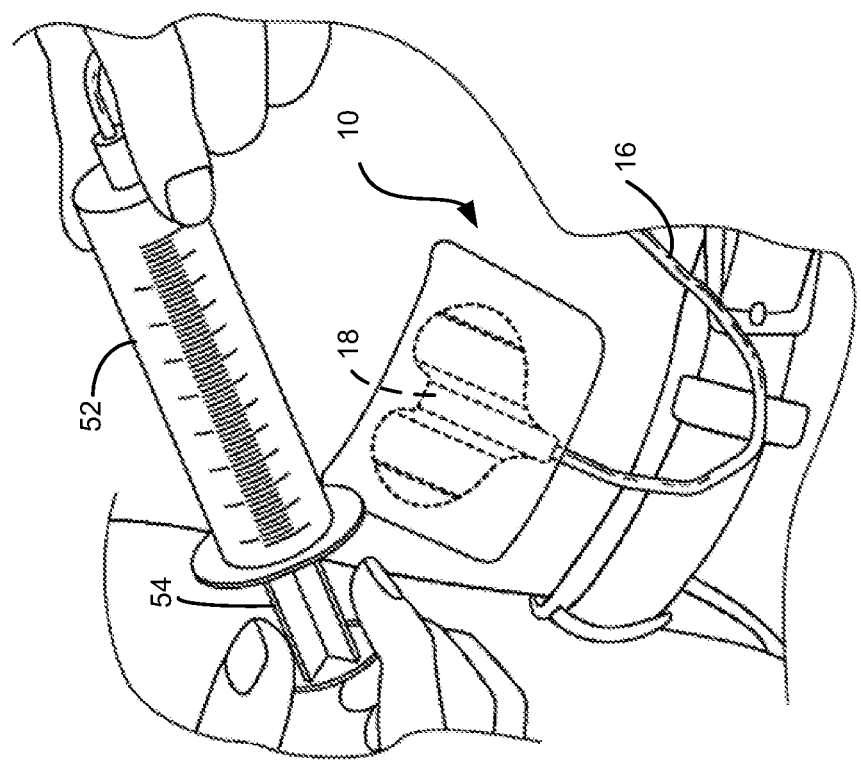
FIG. 7 is a perspective view of the present infusion device during infusion.
Figure 6:
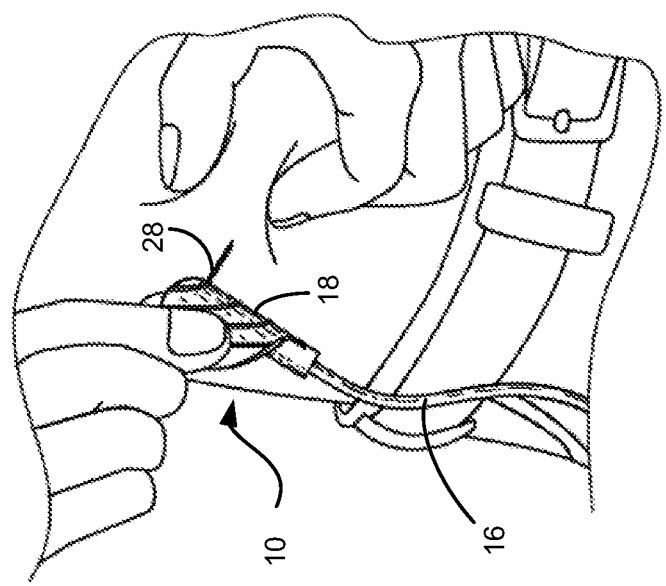
FIG. 6 is a perspective view of the present infusion device being inserted into the infusion site.
Figure 8:
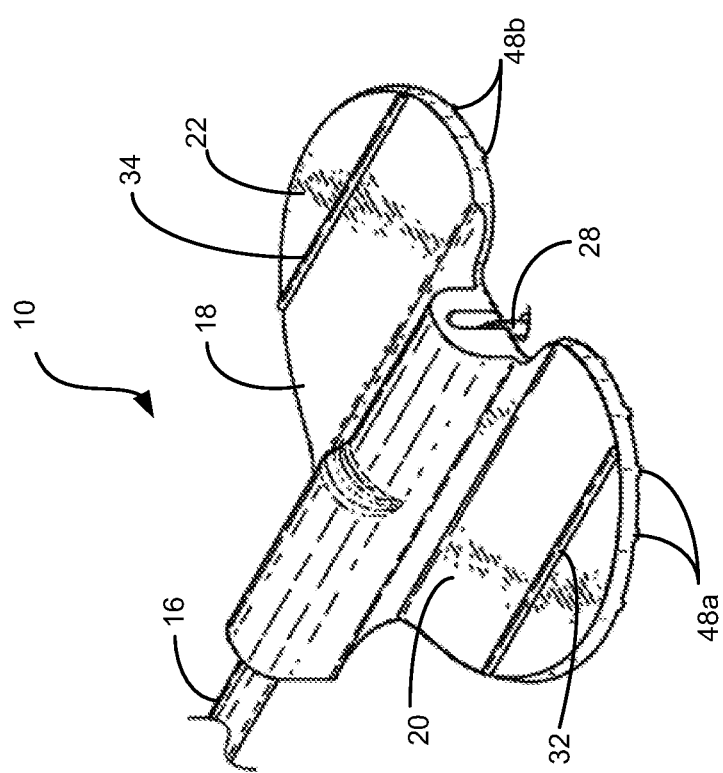
FIG. 8 is an enlarged perspective view of the winged hub after the needle is inserted into the infusion site.

Referring now to FIGS. 5-7, an exemplary use of the present infusion device is illustrated in greater detail. Before inserting the needle 28 into the skin, the user folds the wings 20, 22 back away from the needle 28 and pinches the wings together between two fingers. Then, the user subsequently removes the needle protector 30 from the needle 28, and discards the protector (FIG. 5). In preparation of the insertion, the user pinches an inch of the cleansed skin at the desired infusion site, and inserts the needle 28 with a darting motion, straight into the infusion site at a 90 degree angle (FIG. 6). Next, the user checks a needle placement with a syringe 52 by pulling a plunger 54 backward. If blood is seen in the syringe 52, then the present device 10 is removed and discarded in case of a disposable device. Otherwise, the user repeats the process of preparing the present device 10 and the infusion site. If no blood is seen in the syringe 52, the user secures the needle 28 in place, and starts infusion as directed by a healthcare professional (FIGS. 7-8).

While a particular embodiment of the present infusion device has been shown and described, it will be appreciated by those skilled in the art that changes and modifications may be made thereto without departing from the present disclosure in its broader aspects and as set forth in the following claims.

The invention claimed is:

1. A medical delivery device for delivering a medicinal substance into a user's body, comprising:
a foldable hub having a left wing and a right wing, the hub being attached at one end to a tube, and attached at an opposite end to a needle having a first portion that is coaxial with a longitudinal axis of the tube and a second portion that is bent relative to the longitudinal axis of the tube;
wherein at least one first rib is disposed on the left wing and at least one second rib is disposed on the right wing, such that when the wings are folded back away from the needle and pinched together, the first and second ribs prevent twisting and/or sliding of the wings relative to each other during an insertion of the needle into a user's skin, thereby preventing a breakage of the needle due to undesirable movement of the wings; and
wherein the first rib is spaced in parallel from the longitudinal axis of the tube at a first distance, and the second rib is spaced in parallel from the longitudinal axis at a second distance, the first distance being different from the second distance.

2. The medical delivery device of claim 1, wherein the at least one first and second ribs extend along an entire longitudinal length of a corresponding wing.

3. The medical delivery device of claim 1, wherein each of the at least one first and second ribs is disposed on an upper surface of a corresponding wing such that when the wings are folded, the at least one first and second ribs are directly in contact with the upper surface of a corresponding opposite wing.

4. The medical delivery device of claim 1, wherein the at least one first rib is asymmetrically disposed from the at least one second rib such that the at least one first rib is juxtaposed with the at least one second rib when the wings are folded back away from the needle and pinched together.

5. The medical delivery device of claim 1, wherein a first insertion opening at a first end of a center section of the folding hub is configured for accommodating insertion of the needle, and a second insertion opening at a second opposite end of the center section is configured for accommodating insertion of the tube.

6. The medical delivery device of claim 5, wherein the tube is inserted into the second insertion opening approximately half a length of the center section for reducing a total length of the needle.

7. The medical delivery device of claim 1, further comprising a luer cap configured for receiving the substance at one end, and at an opposite end, being attached to a female luer connector.

8. The medical delivery device of claim 1, further comprising a flexible elongated tube being attached at one end to a female luer connector, and at an opposite end, attached to the foldable hub, and a slide clamp configured for regulating a flow of the substance in the tube by transversely adjusting the clamp relative to a longitudinal axis of the tube.

9. A medical delivery device for administering a medicinal fluid into a subcutaneous tissue of a user's skin, comprising:
a foldable hub having a left wing and a right wing and a center section between the left wing and the right wing, the hub being attached at one end to a tube, and attached at an opposite end to a needle having a first portion that is coaxial with a longitudinal axis of the tube and a second portion that is bent relative to the longitudinal axis of the tube; and
a plurality of continuous, elongated ribs, each rib being diagonally disposed on a bottom surface of each wing in a direction away from a sharp end of the needle, wherein the ribs are configured to inhibit forward movement of the wings toward the sharp end of the needle in a direction parallel to the longitudinal axis of the tube and to allow backward movement of the wings away from the sharp end of the needle in the direction parallel to the longitudinal axis of the tube when the bottom surface of each wing is in contact with a user's skin.

10. The medical delivery device of claim 9, wherein the ribs on the bottom surface of each wing are generally evenly spaced in parallel, and extend along a full diagonal length of a corresponding wing.

11. The medical delivery device of claim 9, wherein the ribs on the bottom surface of each wing are positioned at an angle of approximately 45 degrees relative to a longitudinal axis of the center section of the hub.

12. The medical delivery device of claim 9, wherein a first insertion opening at a first end of the hub is configured for accommodating insertion of the needle, and a second insertion opening at a second opposite end of the hub in fluid communication with the tube is configured for accommodating insertion of the tube.

13. The medical delivery device of claim 11, wherein each rib on the bottom surface of the left wing is inclined or sloped upwardly from a left side of the left wing to a right side of the left wing toward the center section.

14. The medical delivery device of claim 11, wherein each rib on the bottom surface of the right wing is declined or sloped downwardly from a left side of the right wing adjacent the center section to a right side of the right wing.

15. The medical delivery device of claim 9, wherein the plurality of ribs disposed on the bottom surface of the wings are constructed and arranged in a chevron or herringbone pattern.

* * * * *